United States Patent [19]

Laurin

[11] Patent Number: 4,469,835
[45] Date of Patent: Sep. 4, 1984

[54] CONNECTOR MEMBER ADAPTED FOR ULTRAVIOLET ANTIMICROBIAL IRRADIATION

[75] Inventor: Dean G. Laurin, Lake Zurich, Ill.

[73] Assignee: Baxter Travenol Laboratories, Inc., Deerfield, Ill.

[21] Appl. No.: 270,742

[22] Filed: Jun. 5, 1981

[51] Int. Cl.³ .................. C08K 5/00; G01N 21/00; A61L 22/00; C08G 18/28
[52] U.S. Cl. .................. 524/349; 128/912; 138/DIG. 7; 250/455.1; 422/24; 524/120; 524/291; 524/303; 524/304; 524/305; 524/342; 524/404; 524/405; 524/436; 524/437; 604/29; 604/103; 604/283; 604/905
[58] Field of Search ............ 524/349, 350, 291, 342, 524/303–305, 120, 404, 405, 436, 437; 422/24

[56] References Cited

U.S. PATENT DOCUMENTS

| | | | |
|---|---|---|---|
| 2,632,751 | 3/1953 | Anderson | 524/350 |
| 3,026,264 | 3/1962 | Rocklin et al. | 524/342 |
| 3,277,046 | 10/1966 | Listner | 524/305 |
| 3,644,538 | 2/1972 | Starnes | 524/342 |
| 3,917,672 | 11/1975 | Schmidt | 524/281 |
| 3,986,508 | 10/1976 | Barrington | 128/214.2 |
| 4,064,100 | 12/1977 | Hechenbleikner | 524/120 |
| 4,146,530 | 3/1979 | Haeberlein et al. | 524/120 |
| 4,207,229 | 6/1980 | Spivack | 524/120 |
| 4,242,310 | 12/1980 | Greff et al. | 422/300 |
| 4,321,191 | 3/1982 | Minagawa et al. | 524/303 |

Primary Examiner—H. S. Cockeram
Attorney, Agent, or Firm—Garrettson Ellis; Paul C. Flattery

[57] ABSTRACT

A connector member (11) is disclosed for sealed connection with a second connector member (30), to permit sealed flow of material through the joined connector members. The connector member (11) is made of a material selected from the group consisting of aliphatic hydrocarbon resins, aliphatic polyester resins, copolymers of olefins and vinyl acetate, and olefin-acrylate copolymers. The material also contains an effective amount of an antioxidant agent being selected to provide to the material the characteristic of permitting transmission of at least 15 percent of at least one wavelength of ultraviolet radiation having a wavelength between 220 and 300 nanometers through a thickness of 0.003 inch of the material.

36 Claims, 2 Drawing Figures

CONNECTOR MEMBER ADAPTED FOR ULTRAVIOLET ANTIMICROBIAL IRRADIATION

BACKGROUND OF THE INVENTION

This application relates to a connector for systems which must be maintained in as aseptic a condition as possible, while preferably providing a capability for repeated connection and disconnection.

For example, in the technique of continuous ambulatory peritoneal dialysis (CAPD), the patient has a surgically implanted catheter which communicates between the peritoneal cavity and the exterior of the abdomen. Peritoneal dialysis solution is passed into the peritoneal cavity where it dwells for a predetermined period of time. Dialysis of urea and other toxins takes place during this dwell period between the solution and the blood passing through blood vessels in the peritoneum. The peritoneum is the lining of the peritoneal cavity. Thereafter, this peritoneal dialysis solution is drained from the peritoneal cavity via the implanted catheter carrying with it the dialyzed products (urea and other toxins). Fresh dialysis solution is passed into the peritoneal cavity, and this process of infusion and drainage is repeated several times daily, usually four.

In accordance with this invention, it is contemplated to utilize a connector system in which the connecting elements of the system may be exposed to ultraviolet radiation after the connection has been made, while they are still isolated from the remainder of the flow path to the peritoneal cavity. Accordingly, by the ultraviolet treatment, reliable microbial kill of the newly formed connection between a peritoneal dialysis solution container and the peritoneal cavity can be made.

A difficulty arises in that many conventional plastic materials are not suitable for use in making connectors which are capable of both transmitting ultraviolet radiation to an acceptable degree into the interior of each connector, and also withstanding the damaging effects of intense ultraviolet radiation without exhibiting a significant deterioration in physical properties, and ultraviolet transmission characteristics.

For example, in Barrington U.S. Pat. No. 3,986,508, it is suggested to use a medical connector for blood processing utilizing polychlorotrifluoroethylene, followed by sterilization of the connector with ultraviolet radiation. However, fluorinated materials such as this, while exhibiting good transmission of ultraviolet radiation and stability, are drastically more expensive than non-fluorinated, olefin-based polymers.

However, nonfluorinated, olefin-based polymers generally deteriorate readily under irradiation by ultraviolet light.

Furthermore, some common stabilizing materials which are used with olefin-based polymers turn out to be opaque to ultraviolet radiation in the antimicrobial wavelength of between 220 to 300 nanometers, and thus may not be used.

In accordance with this invention, an ultraviolet-irradiatable connector member is disclosed for any desired use, being made of a generally fluorine-free, polyolefin type material which exhibits acceptable transparency to the desired antimicrobial ultraviolet radiation, and at the same time exhibits adequate stability to permit repeated ultraviolet irradiation of connectors made out of such materials.

SUMMARY OF THE INVENTION

In accordance with this invention, a connector member, adapted for a sealed connection with a second connector member to permit the sealed flow of material through the joined connector members, is provided. The connector member is made of a material selected from the group consisting of aliphatic hydrocarbon resins, aliphatic polyester resins, copolymers of olefins and vinyl acetate, olefin-acrylate copolymers, and chlorinated hydrocarbon resins, either in thermoplastic or thermoset form. The material also contains an effective amount of an antioxidant agent dispersed therein, said antioxidant agent being selected to provide to the material the characteristic of permitting transmission of at least 15 percent of at least one wavelength of ultraviolet radiation having a wavelength of between 220 and 300 nanometers through a thickness of 0.003 inch of the material.

Such a connector material may be used, for example, in solution administration sets and implant apparatus in peritoneal dialysis procedures, or other medical or manufacturing procedures where antimicrobial conditions are mandatory. Such connectors may be capable of exposure without significant degradation to ultraviolet energy up to a total amount on the order of 10 watt-$sec/cm^2$ or more, to permit repeated antimicrobial irradiation of connectors by ultraviolet light in accordance with this invention, while using low-cost, fluorine-free materials.

It is generally preferred for the material and dispersed antioxidant of this invention to permit transmission of at least 15 percent of at least one wavelength of ultraviolet radiation in the range of 240 to 280 nanometers. Transmission of ultraviolet radiation in the range of 254 nanometers is most preferred for reasons of economy; radiation at this wavelength provides adequate antimicrobial effects.

It is generally preferred for the antioxidant material used herein to be a phenolic-based antioxidant. The preferred phenolic-based antioxidants are commercially available in various embodiments, and generally constitute hindered phenolics having one or more phenol groups and at least one electron donating group bonded to at least one of the ortho and para positions of the phenol structure. It is also preferred for the phenol structure to be free of bonded sulphur.

Preferably, the antioxidants of this invention carry a phenol group having a pair of tertiary butyl radicals bonded to the positions ortho to the OH of the phenol group. Such materials generally exhibit the requisite antioxidant effect without being too active, to be consumed in the processing of the plastic, while at the same time defining an ultraviolet "window" of relatively low absorption in the range of 240 to 270 nanometers, and particularly at 254 nanometers.

Phenolic-based antioxidants having a phenol group with aliphatic carbon groups bonded in ortho and para relation thereto also tend to exhibit the above desirable combined effect of serving as an oxidation-resistant agent, and having the above-described "window" to ultraviolet radiation in the range specified. Hindered phenolic antioxidant agents are particularly preferred.

Examples of suitable phenol type antioxidant materials include 2,6-di-t-butyl-p-cresol, which is commonly called BHT; 1,3,5-trimethyl-2,4-6-tris[3,5-di-butyl-4-hydroxy-benzyl] benzene; the reaction product of one mole of neopentyl glycol and 4 moles of 3(3,5-di-t- butyl-4-hydroxybenzene) propionic acid; 2,4,6-tri-t-butylphenol; 2,2'-methylenebis[6-t-butyl-4-ethylphenol]; 2,2'-methylenebis[6-t-butyl-p-cresol]; 4,4'-methylenebis[6-t-butyl-o-cresol]; 4,4'-butylidenebis[6-t-butyl-m-cresol]; 2,4,6-tri-styrylphenol; and products of condensation of phenol with aldehydes.

Alternatively, the antioxidant material may be a Phosphorus ester such as a phosphite reaction product with at least one phenyl group having an aliphatic carbon group bonded to at least one of the ortho and para positions; for example, tri-p-nonylphenyl phosphite, 2,6-di-t-butyl-p-tolyl-o-phenylene phosphite, tetrakis[2,4-di-tert-butylphenyl] 4,4'-biphenylenediphosphonite, or disterylpentaerythritoldiphosphite. Such phosphorus compounds may desirably be blended with the phenolic antioxidants.

Phenylene diol based antioxidants may be also utilized for example, p-(benzyloxy)phenol where another electron donating group other than an aliphatic hydrocarbon is provided in the form of the benzyloxy group, to provide the desired antioxidant characteristics. Other similar examples include 2,5-di-t-butyl-hydroquinone; and 2,5-di-5-pentylhydroquinone.

Another antioxidant which may in some circumstances be usable in accordance with this invention is the condensation product of diphenylamine with acetone, and octyl or heptyl substituted diphenylamines.

It is often advantageous to add to the phenolic-type antioxidants a portion of a sulphur-based antioxidant such as disteryl thiodipropionate, or a similar derivative containing other higher alkyl substitutes for the steryl radicals typically containing at least ten carbon atoms each.

Also, hydrides may be added as reducing agents to reverse the effects of oxidation, for example, 0.005 to 2 weight percent of tetraalkyl ammonium borohydrides where the alkyl radicals are methyl or butyl for example, or calcium hydride, magnesium hydride, an alkali metal or alkaline earth metal borohydride such as sodium or magnesium borohydride, or aluminum hydrides also containing the cations mentioned above, such as sodium aluminum hydride or tetramethylammonium aluminum hydride, preferably used with phenolic or other antioxidants.

The concentrations of the antioxidant utilized in the materials of this invention may range from 0.005 to 2 weight percent and preferably about 0.01 to 0.3 weight percent.

A preferred organic resin for use in the material of this invention is poly(ethylene-acrylic acid) in which from about 0.5 to 10 mol percent of acrylic acid is present. The acrylic acid is in the form of a neutral ionomer salt with preferably sodium, but also zinc, magnesium or calcium ions, as may be desired. Such ionomer materials neutralized with sodium or zinc are commercially available at the present time, and are deemed as preferable because of their good stability with low quantities of stabilizer, their optical clarity in the visual spectrum, and low cost. Such clarity does not, of course, necessarily correlate with its clarity in the ultraviolet portion of the spectrum, but formulations made in accordance with this invention also exhibit adequate ultraviolet transmissibility to achieve the purposes of this invention. Types of the above preferred resins may be purchased from the duPont Chemical Company under the name Surlyn. Such material may be stabilized for example, with 0.05 weight percent of 2,6-di-t-butyl-p-cresol.

Other suitable resin materials which may be used in accordance with this invention include low density polyethylene, polypropylene, and copolymers of polypropylene with amounts of polyethylene, for example, about 3 to 10 percent by weight. Ethylene-propylene rubbers may be also used. The commercially available poly(ethylene vinyl acetate) plastics which are also suitable for use in this invention preferably have 10 to 40 weight percent of vinyl acetate units, and thermosetting types containing 45 to 60 percent by weight of vinyl acetate. Vinyl acetate-ethylene rubbers may also be used.

The aliphatic polyesters which may be used in this invention may, for example, by copolymers of cyclohexane dimethanol (sold by Eastman Chemical Company) with aliphatic diacids such as dimer diacids formed from unsaturated fatty acids, or cyclohexane dicarboxylic acids preferably of the para or meta form, optionally with minor amounts of the ortho form to reduce crystallization where desired.

Other polymers such as poly(ethylene-ethyl acrylate) and poly(propylene-ethyl acrylate) are also suitable for use herein.

Other copolymers of ethylene and propylene containing higher contents of ethylene are also suitable, and particularly polyallomers. Furthermore, polymers of high molecular weight olefins such as polymethylpentene may also be used, although that particular material tends to become brittle to some extent upon prolonged exposure to ultraviolet radiation.

Generally, polyethylene and ethylene copolymers are preferred over polypropylene and copolymers of propylene, because of the better stability of the ethylene polymer unit, generally requiring less stabilizer.

Preferably, the polypropylene copolymer and polymers with slow crystal growth may also carry a nucleating agent such as fume silica or calcium stearate to reduce crystal size. Other materials with faster crystal growth such as poly(ethylene-acrylic acid) may not need a nucleating agent.

Additionally, silicone rubber and particularly dimethylpolysiloxane-based, commercially available silicone elastomers may be used to make the connector in whole or in part, if it is acceptable for the particular design of connector to be made of flexible material.

It is generally preferable to use silicone elastomer materials which are cured by the well-known addition curing of silicone-bonded vinyl and silicon-bonded hydrogen in the presence of a platinum catalyst such as chloroplatinic acid. Preferably, the silicones used herein are substantially free of aromatic groups either in the silicone polymer itself, or in the additives. Alternatively, aliphatic peroxide cure systems may be used.

However, fluorosilicones where the fluorine atom is on a beta or gamma carbon to the silicone atom are usable, for example, 3,3,3-trifluoropropylmethylpolysiloxane. These materials are advantageous in that they have good stability. Also, the dimethylpolysiloxane is a preferred material for use herein.

The filler in the silicone elastomer is preferably fume silica or the like, having a particle size of no more than about 20 nanometers and present in less than 30 percent by weight. The presence of increased amounts of silica and larger particles cause substantial scattering of the ultraviolet radiation passing through it.

In the specific embodiment of the connector of this invention, such a silicone material may be advantageously used as a rotating seal.

Commercially available silicone materials meeting the above criteria are available, and may be used.

Typical chlorinated hydrocarbon resins which may be used in this invention include polyvinylidine chloride, plasticized with citrate esters and available as Saran from the Dow Chemical Company, or polyvinyl chloride plasticized with an aliphatic material such as the polyester of glutaric acid and butylene glycol, or the adipate of 1,4 butane diol.

The material utilized in this invention preferably permits transmission of at least 15 percent, and preferably a greater percentage, of at least one wavelength and preferably a band of ultraviolet radiation in the range of 240 to 270 nanometers. An overall ultraviolet exposure of about 0.7 watt.sec/cm$^2$ is often sufficient to provide adequate antimicrobial effects on a connector of this invention having a wall thickness of 0.03 inch.

Preferably, from 0.03 to 0.1 percent by weight of an above described stabilizer is present in the material of the connector of this invention for optimum stability combined with good ultraviolet transmissivity.

DESCRIPTION OF PREFERRED EMBODIMENT

Figure 1:
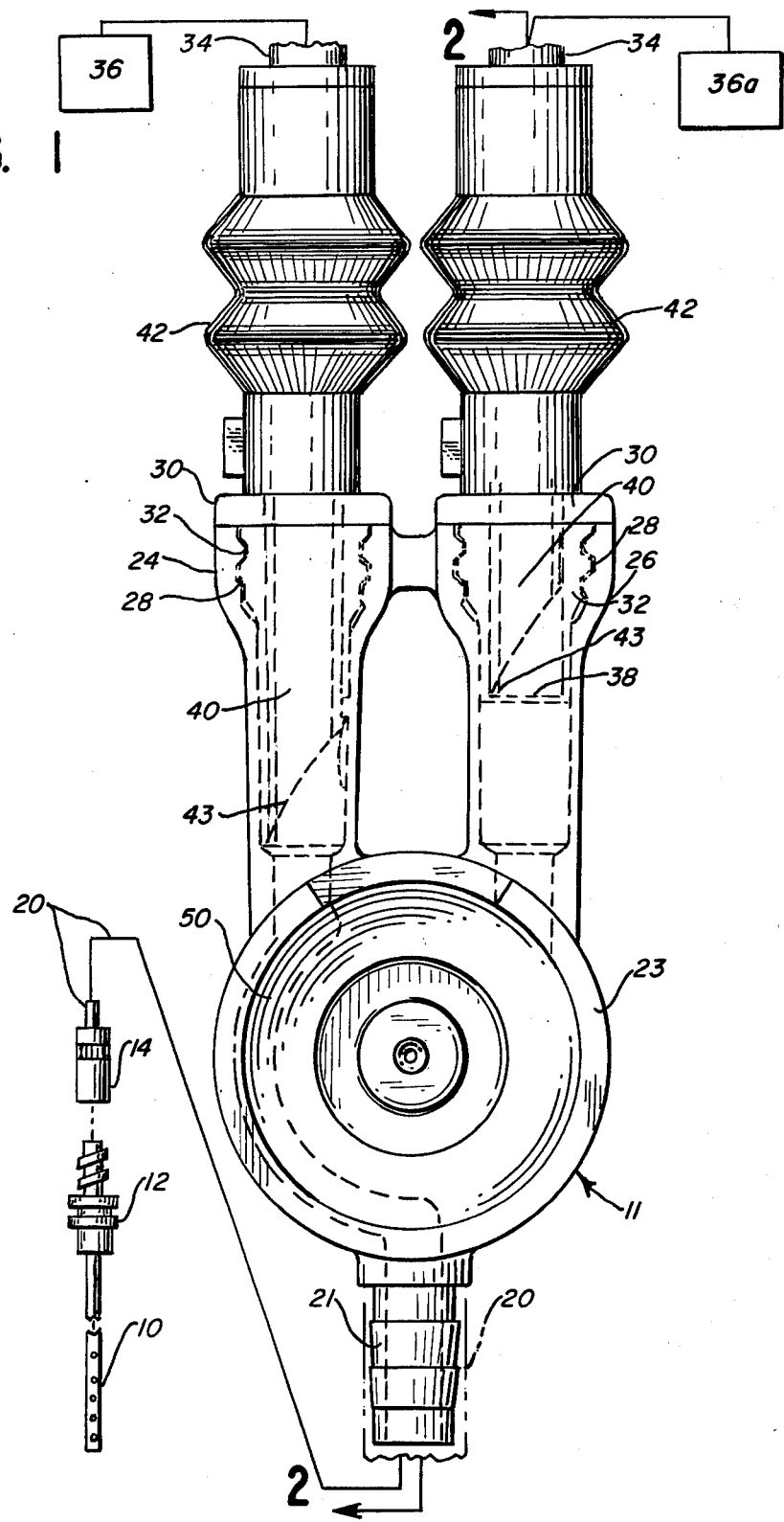
FIG. 1 is a detailed plan view, taken partly in longitudinal section, of a peritoneal dialysis set in accordance with this invention, with some portions thereof being shown schematically and in reduced scale.
Figure 2:
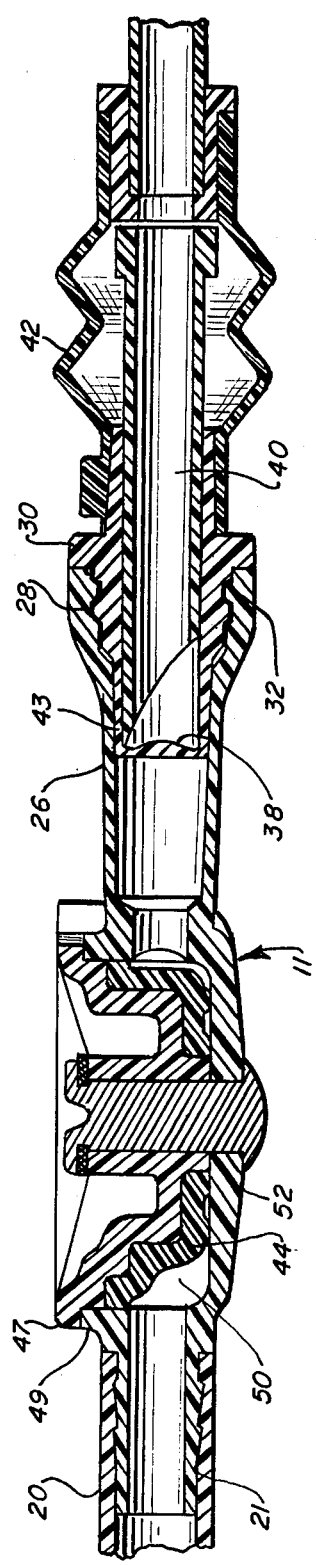
FIG. 2 is a fragmentary, longitudinal sectional view of the multiple-way valve of the set of FIG. 1.

Referring to FIGS. 1 and 2, a connector valve 11 is shown, being made in accordance with this invention to facilitate repeated connection and disconnection during peritoneal dialysis procedures, while substantially suppressing the risk of transmitting infectious bacteria into the peritoneal cavity. The specific design of apparatus may be shown in the concurrently filed patent application of Ralph Kulin, et al. entitled "ANTIMICROBIAL IRRADIATION OF A CONNECTOR FOR CONTINUOUS AMBULATORY PERITONEAL DIALYSIS", Ser. No. 270,743, filed June 5, 1981.

Catheter 10 may be surgically implanted into the peritoneal cavity of the patient, with connector member 12 of conventional design being carried at an end thereof. Connector member 12 and catheter 10 may be constructed to be a generally permanent implant for the patient, with the connector 12 being preferably made of metal such as titanium, for example, and catheter 10 being of durable silicone rubber for permanence and long life. Connector 12 may be of the design disclosed in U.S. application Ser. No. 187,008, filed Sept. 15, 1980.

Tubing 20 permanently communicates with ultraviolet antimicrobial connector valve 11 as shown, with tubing 20 being sealed to port member 21, which may be an integral part of connector valve 11.

At the other end of tubing 20, a second connector 14 is provided, being optionally made of thermoplastic material and proportioned to form a sealed connection with connector member 12, which is carried at the end of catheter 10.

It is generally intended that tubing 20 and connector valve 11 will be connected to connector member 12 at a clinic or a hospital, with the connection operation being performed under aseptic conditions. Tubing 20 and connector valve 11 are then used on a frequent basis for a period of time, for example, about a month without disconnection of connector member 12 and second connector 14. Then, connectors 12, 14 are disconnected, once again at the clinic under aseptic conditions, and a fresh set comprising connector valve 11, tubing 20, and connector 14 are connected under the same aseptic conditions to connector member 12.

The relatively inexpensive set comprising tubing 20 and connector valve 11 may be subjected to ultraviolet radiation to the material of connector valve 11 and other parts becomes excessive.

The ultraviolet radiation technique may be performed in the home by the patient or his family in the period between visits to the clinic when the connection between connector members 12 and 14 is made. This permits the assurance of an antimicrobial connection with the bags of solution and drainage bags for frequent peritoneal dialysis solution exchanges after the user has been trained, without the need for the constant attention of a physician or a trained nurse.

As shown in the drawings, connector valve 11 comprises a housing 23, which may be made of rigid resin material containing an antioxidant agent as described above. Housing 23 further defines a pair of connector arms 24, 26 which may project outwardly from housing 23 at any desired angle, but preferably to form a parallel connection with tubing 20 as shown, or alternatively a T or Y connection.

Connector arms 24, 26 each comprise generally rigid tubular structures defining a receptacle at their outer ends having helical female threads 28 proportioned to receive a penetrating coupler 30 which, in turn, defines projecting helical threads 32 to mate with threads 28 for sealing a penetrating coupler 30 to either connector arm 24 or 26. Each of penetrating couplers 30 is solvent sealed, heat sealed, or the like to flexible tubing 34, which may be made of polyvinyl chloride or the like. Tubing 34, in turn, may connect to a sealed container 36, 36a which may be of conventional design. As can be seen from FIG. 1, connector valve 11 is accordingly in flow connection through each of its connector arms 24, 26 to separate containers 36, 36a. One of the containers 36, 36a may serve as a source of peritoneal dialysis solution, while the other of the containers may be empty, and serves as a receptacle for spent peritoneal dialysis solution. For example, container 36a may be a collapsible bag which the patient can carry under his clothes.

Each of the penetrating couplers 30 has a diaphragm 38, preferably at its inner end, as shown. Freely movable, hollow spike member 40 is also provided in each of the coupler members 30. Hollow spike member 40 may be pushed inwardly by manual manipulation of plastic bellows portions 42 of tubing 34, to cause the pointed end 43 of spike 40 to rupture diaphragm 38, when it is desired to open a connection between container 36 and connector 11. Hollow spike member 40 is shown in phantom in connector arm 26 before puncture of membrane 38, and shown in phantom in connector arm 24 after puncture of member 38.

Connector valve 11 defines a preferably elastomeric stop cock seal member 44, which is a rotatable member of generally circular structure, fitting within cylindrical housing 23 as part of connector valve 11, and carried by rotatable outer closure 47.

Groove 50 is shown in phantom in FIG. 1, and is defined by one face of stop cock seal member 44, to rotate with the rotation of the seal member 44, to provide an on-off flow connection between tubing 20 and connector arms 24, 26. Accordingly, when diaphragm 38 is ruptured, peritoneal dialysis solution from container 36 can pass through groove 50 into tubing 20, and thus into catheter 10 and the peritoneal cavity of the patient. Groove 50 may then be rotated so that no flow can pass through the connector valve 11.

Thereafter, when it is desired to drain the spent peritoneal dialysis solution from the patient, groove 50 may be rotated so that groove 50 connects between tubing 20 and connector arm 26. The spike 40 of connector arm 26 may be advanced as in the previous manner to open a flow path between the patient's peritoneal cavity and the bag 36a connected therewith for receiving the drained peritoneal dialysis solution.

Thereafter, groove 50 can be rotated again so that an additional portion of peritoneal dialysis solution may pass from a new bag 36 into the peritoneal cavity of the patient.

When it is desired to disconnect one or more of the penetrating couplers 30, groove 50 is simply rotated to isolate the appropriate connector arm 24 and/or 26 from groove 50, so that any contamination remains isolated in the respective connector arm upon opening.

As long as there is the possibility of the existence of contamination in either of connector arms 24, 26, groove 50 and seal member 44 should remain in a position to isolate that connector arm.

The structure of this invention may be then reconnected to a new projecting coupler 30 and its attached container 36 or 36a. Then, before groove 50 is rotated, connector valve 11, including connector arms 24, 26, is exposed to an ultraviolet radiation source, preferably of a wavelength of about 254 nanometers, the antimicrobial wavelength of ultraviolet light, with the radiation passing through bottom wall 52 of housing 23 and other directions. An overall dosage of about 0.6 watt.sec/cm$^2$ or more may be provided for each irradiation with the ultraviolet radiation also passing through the walls of projecting connector arms 24, 26. As stated above, these structures may comprise an integral piece, and they are made of a material having good physical properties and substantial transparency to the ultraviolet radiation used. As a result of this, the area within housing 23 and projecting arms 24, 26 are subjected to the antimicrobial effects of ultraviolet radiation including the outside surfaces of penetrating couplers 30.

It is preferred for the ultraviolet radiation to be applied to both the top and bottom of the connector valve 11, particularly in the area of the coupler members 30. If desired, tubing 20 may also be made of a material as described herein and exposed to ultraviolet radiation. Otherwise, it may be made of polyvinyl chloride or the like.

The exterior surfaces of diaphragms 38 should also receive the antimicrobial effect of ultraviolet radiation. To facilitate this, diaphragm 38 may be positioned at the outer end of coupler 30, so that all nonsterile surfaces are easily exposable to ultraviolet light. It is to be understood that the interior portions of coupler member 30 remain sterile as long as diaphragm 38 is not broken, so the couplers 30 do not have to made of an ultraviolet transparent material, although they may be so made if desired.

Furthermore, groove 50 is exposed along its entire length to bottom wall 52 of housing 23, so it will receive antimicrobial radiation as well as the entire area inside of housing 23.

Stop cock seal member 44 may, as shown in FIG. 2, comprise outer closure 47, attached to housing 23 by an interlocking flange structure 49 of conventional design, to provide a sealed but rotatable structure. Also, seal member 44 may be provided underneath closure 47, and attached thereto, being preferably made of silicone rubber to serve as a seal.

The connector members of this invention may be of any desired design, with the multiple-way valve connector structure as shown being only one particularly contemplated, but preferred, design. For example, luer-type connectors having flexible tubing that is pinched closed, with the ultraviolet irradiation taking place after connection but before opening the pinch closures, constitutes another type of design in which the couplers of this invention may be used. Also, internal breakaway seals may be used of the general type shown in U.S. Pat. No. 4,181,140 in place of diaphragms 38.

Also, the connector of this invention may be utilized in procedures other than peritoneal dialysis, to facilitate the antimicrobial effects of ultraviolet radiation in other products and processes, such as parenteral solution administration in general and the like. Connector valves made with the materials as described in this invention may be reconnected and disconnected, with ultraviolet radiation providing repeated, reliable antimicrobial effect in the connector valve interior.

The ultraviolet irradiation may take place while spent peritoneal dialysis solution is flowing into bag 36a, to save time in the process, so that fresh peritoneal dialysis solution may pass from bag 36 into the patient's peritoneal cavity promptly after the drainage step. It is also desirable, but not necessary, for the ultraviolet irradiation to continue while the solution is passing from bag 36 into the patient's peritoneal cavity.

Accordingly, connectors made with the materials as described in this invention may be reconnected and disconnected, with ultraviolet radiation providing repeated antimicrobial effects in the connector interiors. Thereafter, the flow path of the connector are opened, for example, to permit the transfer of peritoneal dialysis solution to and from the peritoneal cavity on a repeated, intermittent basis.

Certain materials used herein are autoclavable so that they may be initially steam sterilized, if desired. They may also be sterilized by radiation or ethylene oxide.

Examples of specific materials usable in accordance with this invention to make connectors are as follows:
  (a) Poly(ethylene-zinc acrylate) (Surlyn containing 0.05 weight percent of 2,6-di-t-butyl-p-cresol, as provided by the manufacturer.
  (b) Polypropylene (Rexene 23T2) containing 0.05 weight percent of 1,3,5-trimethyl-2,4,6-tris[3,5-dibutyl-4-hydroxybenzyl] benzene.
  (c) Poly(ethylene-vinyl acetate) containing 28 weight percent vinyl acetate, containing 0.05 weight percent of the same stabilizer as in (b) above.
  (d) A flexible polyvinyl chloride formulation containing: 100 parts by weight of PVC (PVC 500 of Diamond Shamrock); 75 parts by weight of polybutyl adipate (Monsanto 334FM); 0.2 parts of calcium-zinc stearate stabilizer and 0.1 part of the same stabilizer as in (b) above.

The above has been offered for illustrative purposes only, and is not intended to limit the invention of this application, which is as defined in the claims below.

That which is claimed is:

1. A connector member communicating with flow tubing and adapted for sealed, aseptic connection with a second connector member to permit the sealed flow of material through the joined connector members, said connector member being made of a material selected from the group consisting of aliphatic hydrocarbon resins, aliphatic polyester resins, copolymers of olefins and vinyl acetate, olefin-acrylate copolymers, and chlorinated aliphatic hydrocarbon resins, said material containing an effective amount of an antioxidant agent dispersed therein, said antioxidant agent being selected to provide to the material the characteristic of permitting transmissions of at least 15 percent of at least one wavelength of ultraviolet radiation having a wavelength between 220 and 300 nanometers through a thickness of 0.003 inch of the material.

2. The connector member of claim 1 in which said material and dispersed antioxidant permits transmission of at least 15 percent of at least one wavelength of ultraviolet radiation in the range of 240 to 270 nanometers.

3. The connector member of claim 1 in which said antioxidant material is a phenolic-based antioxidant.

4. The connector member of claim 1 in which said antioxidant material comprises a phenolic-based antioxidant having a phenol group with aliphatic carbon groups bonded in ortho and para relation thereto.

5. The connector of claim 1 in which said antioxidant material is a phosphorous ester of at least 1 phenol group having an aliphatic carbon group bonded to at least one of the ortho and para positions.

6. The connector of claim 1 in which said antioxidant material is a phenolic-based antioxidant having a phenol group and at least 1 electron donating group bonded to at least one of the ortho and para positions, said phenol structure being free of bonded sulphur.

7. The connector of claim 1 in which said dispersed antioxidant material comprises 1,3,5-trimethyl-2,4,6-tris[3,5-di-t-butyl-4-hydroxybenzyl]benzene.

8. The connector of claim 1 in which said dispersed antioxidant comprises the reaction product of 1 mole of neopentyl glycol and 4 moles of 3,5-di-t-butyl-4-hydroxybenzene propionic acid.

9. The connector of claim 1 in which said dispersed antioxidant comprises 2,6-di-t-butyl-p-cresol.

10. The connector of claim 1 in which said material and dispersed antioxidant permits transmission of at least 15 percent of at least one wave length of ultraviolet radiation in the range of 240 to 260 nanometers with an overall ultraviolet exposure of about 0.6 watt.sec/cm$^2$.

11. The connector member of claim 1 in which said antioxidant agent comprises a phenolic-based antioxidant having a phenol group with aliphatic carbon atoms bonded in ortho and para relation thereto, there also being present a dialkyl thiodipropionate in which the alkyl radicals each contain at least ten carbon atoms.

12. The connector of claim 1 in which said antioxidant agent is a dialkyl pentaerythritol diphosphite where the alkyl radicals each contain at least ten carbon atoms.

13. The connector of claim 1 in which the material contains a reducing agent selected from the group consisting of tetraalkyl ammonium borohydrides, the borohydrides of the alkaline and alkaline earth metals, the hydrides of the alkaline earth metals, and aluminum hydride salts.

14. The connector of claim 1 which is capable of exposure without significant degradation to a total exposure of 10 watt.sec/cm$^2$ of ultraviolet radiation.

15. The connector of claim 1 in which from 0.005 to 2 weight percent of said antioxidant is present in said material.

16. A method of forming a connector member which comprises mixing with a material selected from the group consisting of aliphatic hydrocarbon resins, aliphatic polyester resins, copolymers of olefins and vinyl acetate, olefin-acrylate copolymers, and chlorinated aliphatic hydrocarbon resins, an antioxidant agent to disperse said agent in the material, said antioxidant agent being selected to provide to the material the characteristic of permitting transmissions of at least 15 percent of at least one wavelength of ultraviolet radiation having a wavelength between 220 and 300 nanometers through a thickness of 0.003 inch of the material, and thereafter forming said material plus antioxidant agent into a connector member which is adapted for sealed, aseptic connection with a second connector member, to permit the sealed flow of material through the joined connector members.

17. The method of claim 16 in which said material and dispersed antioxidant permits transmission of at least 15 percent of at least one wavelength of ultraviolet radiation in the range of 240 to 270 nanometers.

18. The method of claim 16 in which said material is a phenolic-based antioxidant.

19. The method of claim 16 in which said antioxidant material comprises a phenolic-based antioxidant having a phenyl group with aliphatic carbon groups bonded in ortho and para relation thereto.

20. The method of claim 16 in which said antioxidant material is a phosphorous ester of at least one phenyl group having an aliphatic carbon group bonded to at least one of the ortho and para positions.

21. The method of claim 16 in which said antioxidant material is a phenolic-based antioxidant having a phenyl group and at least one electron donating group bonded to at least one of the ortho and para positions, said phenol group being free of bonded sulphur.

22. The method of claim 16 in which said dispersed antioxidant material comprises 1,3,5-trimethyl-2,4,6-tris-[3,5-di-t-butyl-4-hydroxybenzyl]benzene.

23. The method of claim 16 in which said dispersed antioxidant comprises the reaction product of one mole of neopentyl glycol and four moles of 3,5-di-t-butyl-4-hydroxybenzene propionic acid.

24. The method of claim 16 in which said dispersed antioxidant comprises 2,6-di-t-butyl-p-cresol.

25. The method of claim 16 in which from 0.005 to 2 weight percent of said antioxidant is present in said material.

26. The connector member of claim 1 in which said material is a copolymer of propylene and ethylene.

27. The connector member of claim 1 in which said material is poly(ethylene-vinyl acetate) in which the vinyl acetate content is from 10 to 40 percent by weight.

28. The connector member of claim 1 in which said material is poly(ethylene-acrylic acid) in which from 0.5 to 10 mole percent of acrylic acid is present, said acrylic acid being in the form of a salt with a metal selected from the group consisting of sodium, magnesium, calcium and zinc.

29. The connector of claim 1 in which said material is a copolymer of ethyl acrylate and an olefin selected from the group consisting of ethylene and propylene.

30. The connector of claim 1 in which said material is polyvinyl chloride plasticized with an aliphatic polyester plasticizer.

31. The connector of claim 1 in which said material is a polyvinylidine chloride plastic.

32. A connector member adapted for sealed connection with a second connector member to permit the sealed flow of material through the joined connector members, said connector member comprising poly-(ethylene-acrylic acid) in which from 0.5 to 10 mole percent of acrylic acid is present, said acrylic acid being in the form of a neutral salt with metal selected from the group consisting of sodium, magnesium, calcium, and zinc, containing an effective amount of a hindered phenolic antioxidant agent therein, said antioxidant agent being selected to provide the characteristic of permitting transmission of at least 15 percent of at least 1 wavelength of ultraviolet radiation, having a wavelength between 240 to 270 nanometers through a thickness of 0.0013 inch of the material.

33. The connector member of claim 32 in which said antioxidant agent is 2,6-di-t-butyl-p-cresol.

34. The connector member of claim 32 in which from 0.005 to 0.3 percent by weight of said antioxidant agent is present in said poly(ethylene-acrylic acid).

35. The connector member of claim 32 which is capable of exposure without significant degradation to a total exposure of 10 watt.sec/cm$^2$ of ultraviolet radiation.

36. The connector of claim 32 in which said neutral salt comprises a salt of sodium.

* * * * *